United States Patent [19]

Mohan et al.

[11] Patent Number: 5,264,621
[45] Date of Patent: Nov. 23, 1993

[54] ANTI-VIRUS AGENT

[75] Inventors: Prem Mohan, Willowbrook, Ill.; Masanori Baba, Fukushima, Japan

[73] Assignee: Sanyo-Kokusaku Pulp Co., Ltd., Tokyo, Japan

[21] Appl. No.: 830,922

[22] Filed: Feb. 4, 1992

[30] Foreign Application Priority Data

Oct. 25, 1991 [JP]  Japan .................................. 3-307026

[51] Int. Cl.$^5$ ...................... C07C 211/18; A01N 37/18
[52] U.S. Cl. ........................................ 562/52; 514/618
[58] Field of Search ........................... 562/52; 514/618

[56] References Cited

PUBLICATIONS

Antiviral Research, Suppl. I, Apr. 1991, p. 61, P. Mohan, et al., "Structurnal Design and Anti-HIV-1 Evaluation of Novel Naphthalenedisulfonic Acid Derivatives".

*Primary Examiner*—Paul J. Killos
*Assistant Examiner*—Joseph Conrad, III
*Attorney, Agent, or Firm*—Oblon, Spivak, McClelland, Maier & Neustadt

[57] ABSTRACT

Development of medicament having anti-virus activity, particularly anti-HIV (anti-human immunodeficiency virus) activity. An anti-virus agent comprising bis-naphthalenedisulfonic acids having aliphatic spacer represented by the formula (1) and their physically usable salts.

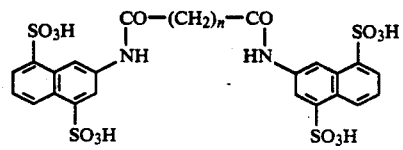

1 Claim, No Drawings

ANTI-VIRUS AGENT

BACKGROUND OF THE INVENTION

The present invention relates to an anti-virus agent, particularly an anti-human immunodeficiency virus agent (hereinafter, abbreviated as "anti-HIV agent") aiming at prophylaxis and treatment of AIDS and, in more detail, relates to an anti-virus agent having bis-naphthalenedisulfonic acids having aliphatic spacer or their salts as effective ingredients.

Recently, same diseases caused by newly confirmed virus have come to appear and to be found, and so prophylaxis and treatment of virus diseases have increasingly become necessary. Among them, it is known that particularly HIV (human immunodeficiency virus) is a human retrovirus and specifically infects the helper T-cells of human to cause the immunoimpediment. Through this infection, persons get into the acquired immune deficiency syndrome and, as a result, bring death on themselves because of losing the resistance to various external infections.

Today, various compounds are proposed as anti-AIDS virus agents and developed as medicinal drugs. Among them, only one that is said to be clinically effective and actually commercialized is azido thymidine (AZT) having impeditive action to reverse transcriptase. However, it has side effects such as inhibition of the growth of bone marrow cells and it has no inhibitory activity for the fusion (formation of giant cells) of infections cells with noninfectious cells, which is a cause of destruction of immune T-cells playing an important role in the progress of AIDS symptoms. Further, now, anti-HIV agents of nucleic acid derivatives such as DDI and DDG are investigated as similar impeders to reverse transcriptase, but so much effective impeders of non-nucleic acid type to reverse transcriptase have not been found.

As the drugs having impeditive activity to infection, polysaccharide sulfates such as dextran sulfate are known (Japanese Unexamined Patent Publication No. Hei 2-7577), but they are not put into practice. It is probable that, because sulfonic groups form ester linkages with hydroxyl groups of sugar in them and they are susceptible to the action of sulfatase in blood to be immediately desulfonated, they cannot exert the effect. Moreover, as the high-molecular sulfonate linked sulfonic groups directly to carbon atoms, there is lignin sulfonate (Japanese Unexamined Patent Publication No. Hei 3-120223), but this is a polymer, phenylpropanol being polymerized at random, and has a drawback that the structure and the position of sulfonic groups introduced are not distinct.

As a result of diligent investigations to solve the problems aforementioned, the inventors have found that bisnaphthalenedisulfonic acids having aliphatic spacer and their salts have excellent anti-virus activity, particularly anti-HIV activity, leading to the completion of the invention.

SUMMARY OF THE INVENTION

The invention provides an anti-virus agent, particularly an anti-HIV agent comprising bisnaphthalenedisulfonic acids having aliphatic spacer or their physiologically usable salts.

DETAILED DESCRIPTION OF THE INVENTION

For the spacer for bisnaphthalenedisulfonic acid and its salt, aliphatic compound is suitable and it is considered that compound with $n = 1-20$ exhibits higher activity. If the spacer is too long, the activity of compound is lowered because of relationship in its position.

Different from the sulfated polysaccharides known hitherto, the sulfonates of the invention have sulfonic groups linked directly to carbon atoms. With sulfated polysaccharides known hitherto, oxygen atom and sulfonic groups are linked forming esters, hence they have the possibility to undergo the action of sulfatase in blood to be immediately desulfonated and to lose activity. Whereas, with the inventive articles, carbon atoms are directly sulfonated, hence it is anticipated that they undergo no action of sulfatase to increase the stability in blood. However, the spacer mentioned here means that it plays a role of maintaining distance between the monomer having physiological function and has no physiological function by itself.

Further, the sulfonates of the invention have the inhibitory ability for the formation of giant cells and the impeditive activity to reverse transcriptase, hence they are very effective anti-virus agents.

In following, the invention will be illustrated in detail based on the examples, but the invention is not confined to these.

EXAMPLE 1

Of 3,3'-[1,10-decanediyl-bis(carbonylamino)]-bis(1,5-naphthalenedisulfonic acid) represented by formula 2, the anti-HIV activity was determined by methods as shown below. As the anti-HIV activity, the inhibition of cell destruction due to HIV, the impeditive activity to reverse transcriptase and the inhibitory activity for the formation of giant cells were tested.

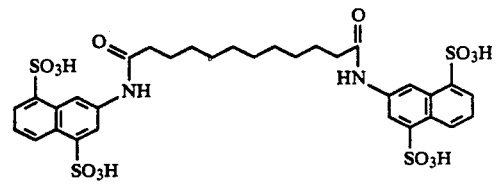

Measurement methods of anti-HIV activity

1. Inhibitory effect on the destruction of T-cells due to HIV

Various concentrations of 3,3'-[1,10-decanediyl-bis(carbonylamino)]-bis(1,5-naphthalenedisulfonc acid) were added to each medium suspended $1 \times 10^5$ cells/ml of MT-4 cells, which was infected with HTLV-III$_B$ or HIV-1$_{HE}$. Infection was made at an infection number of MOI=0.02. Then, after cultured for 4 days at 37° C., the number of surviving cells was quantitatively determined by dyeing surviving cells with MTT dye. Moreover, at the same time, by dyeing also non-infected cells with MTT dye, the toxicity of sample to cells was calculated.

As a result of having measured the activity as above, 3,3'-[1,10-decanediyl-bis(carbonylamino)]-bis(1,5-naphthalenedisulfonic acid) showed the 50% effective antiviral concentration (EC$_{50}$), 50% toxic concentration (CC$_{50}$) and selective toxicity (T.I.=CC$_{50}$/EC$_{50}$) in each system as shown in Table 1.

TABLE 1

| No. | Virus strain | Cell | EC$_{50}$[a] | CC$_{50}$[b] | T.I.[c] |
|---|---|---|---|---|---|
| 1 | HTLV-III$_B$ | MT-4 | 46 | 383 | 8.3 |
| 2 | HIV-1$_{HE}$ | MT-4 | 40.7 | 500 | 12.3 |

[a] EC$_{50}$ = Effective concentration for inhibition of 50% cells (μg/ml)
[b] CC$_{50}$ = 50% toxic concentration (μg/ml)
[c] T.I. = Selective toxicity (CC$_{50}$/EC$_{50}$)

2. Impeditive activity to reverse transcriptase

A reaction mixture of 50 mM of tris hydrochloric acid (pH 8.4), 2 mM of dithiothreitol, 100 mM of potassium chloride, 10 mM of magnesium chloride, 0.1% Triton X-100, 1 μCi of methyl-$^3$H dTTp, 0.01 A$_{260}$ unit of poly(A).oligo(dT), 3,3'-[1,10-decanediyl-bis(carbonylamino)]-bis(1,5-naphthalenedisulfonic acid) and 0.05 U of enzyme was reacted for 30 minutes at 37° C. Then, 5% trichloroacetic acid were added and the radioactivity in precipitates formed was determined.

As a result of having measured the impeditive activity to reverse transcriptase as above, the 50% inhibitory concentration (IC$_{50}$) of 3,3'-[1,10-decanediyl-bis-(carbonylamino)]-bis(1,5-naphthalenedisulfonic acid) was 26.6 μM.

3. Inhibition of the formation of giant cells

MOLT-4 cells infected with HTLV-III$_B$ and MOLT-4 cells without infection were cultured each in same number (5×10$^4$) in medium with 3,3'-[1,10-decanediyl-bis(carbonylamino)]-bis(1,5-naphthalenedisulfonic acid) added and, after cultured for 24 hours, the number of giant cells formed was counted under microscope.

As a result, the inhibitory activity thereof against formation of giant cells was recognized.

We claim:

1. A compound of the formula (1)

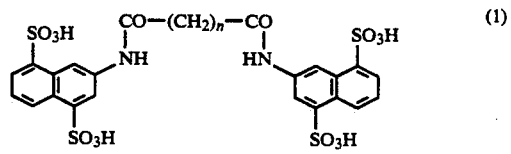

wherein n is 10, and physiologically acceptable salts thereof.

* * * * *

UNITED STATES PATENT AND TRADEMARK OFFICE
CERTIFICATE OF CORRECTION

PATENT NO. : 5,264,621
DATED : November 23, 1993
INVENTOR(S) : PREM MOHAN ET AL

It is certified that error appears in the above-indentified patent and that said Letters Patent is hereby corrected as shown below:

On the title page: Item [56]

Masthead page, line 2 under PUBLICATIONS, "Structurnal Design" should read --"Structural Design--.

Column 2, line 53, "1,5-naphthalenedisulfonc" should read --1,5-naphthalenedisulfonic--.

Column 3, line 24, "[1,10-decanediyl-bis-(" should read --[1,10-decanediyl-bis(--.

Signed and Sealed this

Eighteenth Day of October, 1994

Attest:

BRUCE LEHMAN

Attesting Officer

Commissioner of Patents and Trademarks